US00PP12677P2

(12) United States Plant Patent
Campo

(10) Patent No.: US PP12,677 P2
(45) Date of Patent: Jun. 4, 2002

(54) DRACAENA PLANT NAMED 'JELLE'

(75) Inventor: Jan Campo, Naaldwijk (NL)

(73) Assignee: Campo International B.V., Naaldwijk (NL)

( * ) Notice: Subject to any disclaimer, the term of this patent is extended or adjusted under 35 U.S.C. 154(b) by 0 days.

(21) Appl. No.: 09/563,941

(22) Filed: May 4, 2000

(51) Int. Cl.[7] ..... A01H 5/00
(52) U.S. Cl. ..... Plt./383
(58) Field of Search ..... Plt./383

(56) References Cited

PUBLICATIONS

UPOV–ROM GTITM Computer Database 2001/01, Feb. 6, 2001, GTI Jouve Retrieval Software, Citation for 'Jelle'.*

* cited by examiner

*Primary Examiner*—Bruce R. Campell
*Assistant Examiner*—June Hwu
(74) *Attorney, Agent, or Firm*—C. A. Whealy

(57) ABSTRACT

A distinct cultivar of Dracaena plant named 'Jelle', characterized by its upright and columnar growth habit; leaves all the way from the bottom to top of plant; green and yellowish green variegated leaves that are thick, strong and leathery; and excellent post-production longevity.

2 Drawing Sheets

BACKGROUND OF THE INVENTION

The present invention relates to a new and distinct cultivar of Dracaena plant, botanically known as *Dracaena fragrans* Stedneri., and hereinafter referred to by the cultivar name Jelle.

The new cultivar was discovered by the Inventor in a production field of Dracaena in Costa Rica as a naturally-occuring mutation of an unidentified selection of *Dracaena fragrans* Stedneri. The new Dracaena was observed as a single plant in a group of plants of the parent selection in February, 1994. This plant was selected on its unique leaf variegation pattern as plants of the parent selection do not have variegated leaves.

Asexual propagation of the new cultivar by cuttings at Naaldwijk, The Netherlands, has shown that the unique features of this new Dracaena plant are stable and reproduced true to type in successive generations of asexual propagation.

The new Dracaena has not been observed under all possible environmental conditions. The phenotype may vary somewhat with variations in environment such as temperature and light intensity, without, however, any variance in genotype.

SUMMARY OF THE INVENTION

The following traits have been repeatedly observed and are determined to be the unique characteristics of 'Jelle'. These characteristics in combination distinguish 'Jelle' as a new and distinct cultivar:

1. Upright and columnar growth habit.
2. Leaves from bottom to top of plant.
3. Green and yellowish green variegated leaves that are thick, strong and leathery.
4. Excellent post-production longevity.

The new Dracaena can be compared to plants of *Dracaena fragrans* 'Massangeana', not patented. However in side-by-side comparisons conductin in Naaldwijk, The Netherlands, plants of the new Dracaena forms leaves all the way from the base of the plant to the top of the plant whereas plants of 'Massangeana' has leaves only at the top of the plant. In addition, plants of the new Dracaena are more cold-tolerant than plants of 'Massangeana'.

DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Dracaena.

The first photograph on the first sheet comprises a top perspective view of a typical potted plant of 'Jelle'.

The photograph at the top of the second sheet comprises a close-up view of a stem of a typical plant of 'Jelle'.

The photograph at the bottom of the second sheet comprises a close-up view of typical leaves of 'Jelle' showing the variegation pattern.

DETAILED BOTANICAL DESCRIPTION

The following observations, measurements and comparisons describe plants grown in Naaldwijk, The Netherlands, in a glass-covered greenhouse with day temperatures about 22 to 23° C., night temperatures about 20° C., and light levels of about 2,000 to 3,000 foot-candles. Plants were about seven months old and were grown in 20-cm containers. In this description, color references are made the The Royal Horticultural Society Colour Chart except where general terms of ordinary dictionary significance are used.

Botanical classification: *Dracaena fragrans* Stedneri. cultivar Jelle.

Parentage: Naturally-occurring whole plant mutation of an unidentified selection of *Dracaena fragrans* Stedneri., not patented.

Propagation:

*Method.*—By cuttings.

*Time to initiate roots.*—About 14 and 18 days during the summer and winter at 22° C., respectively.

*Root description.*—Numerous thick and fleshy roots.

Plant description:

*Plant shape.*—Upright, columnar, symmetrical.

*Usage.*—Appropriate for 10 to 25-cm containers.

*Plant height.*—About 82 cm from soil level to top of leaf plane.

*Plant diameter or spread.*—About 77 cm.

*Plant vigor.*—Moderate.

*Growth rate.*—Moderate to rapid.

*Crop time.*—About seven months are usually required from planting of a young plant to a finished plant in a 20-cm container.

*Foliage description.*—Quantity of leaves per finished plant: About 39. Arrangement: Alternate. Leaf shape: Linear, narrowly elliptic. Leaf apex: Abruptly acute. Leaf attachment: Decurrent, sessile. Leaf margin: Entire. Leaf texture, upper and lower surfaces: Leathery, smooth, glabrous. Leaf venation: Parallel. Leaf size: Length: About 21 to 32 cm. Width: About 5 to 7.5 cm. Leaf color: Longitudinally variegated. Upper surface: Margins are green, between 137A and 137C. Central area with yellowish green longitudinal stripes, between 145A and 144C. Lower surface: Margins are green, closest to 138B. Central area with yellowish green longitudinal stripes, 145B.

Flower description: Flowers have not been observed on plants of the new Dracaena.

Disease resistance: Under commercial conditions, resistance to pathogens common to Dracaenas has not been observed.

It is claimed:

1. A new and distinct cultivar of Dracaena plant named 'Jelle' as illustrated and described.

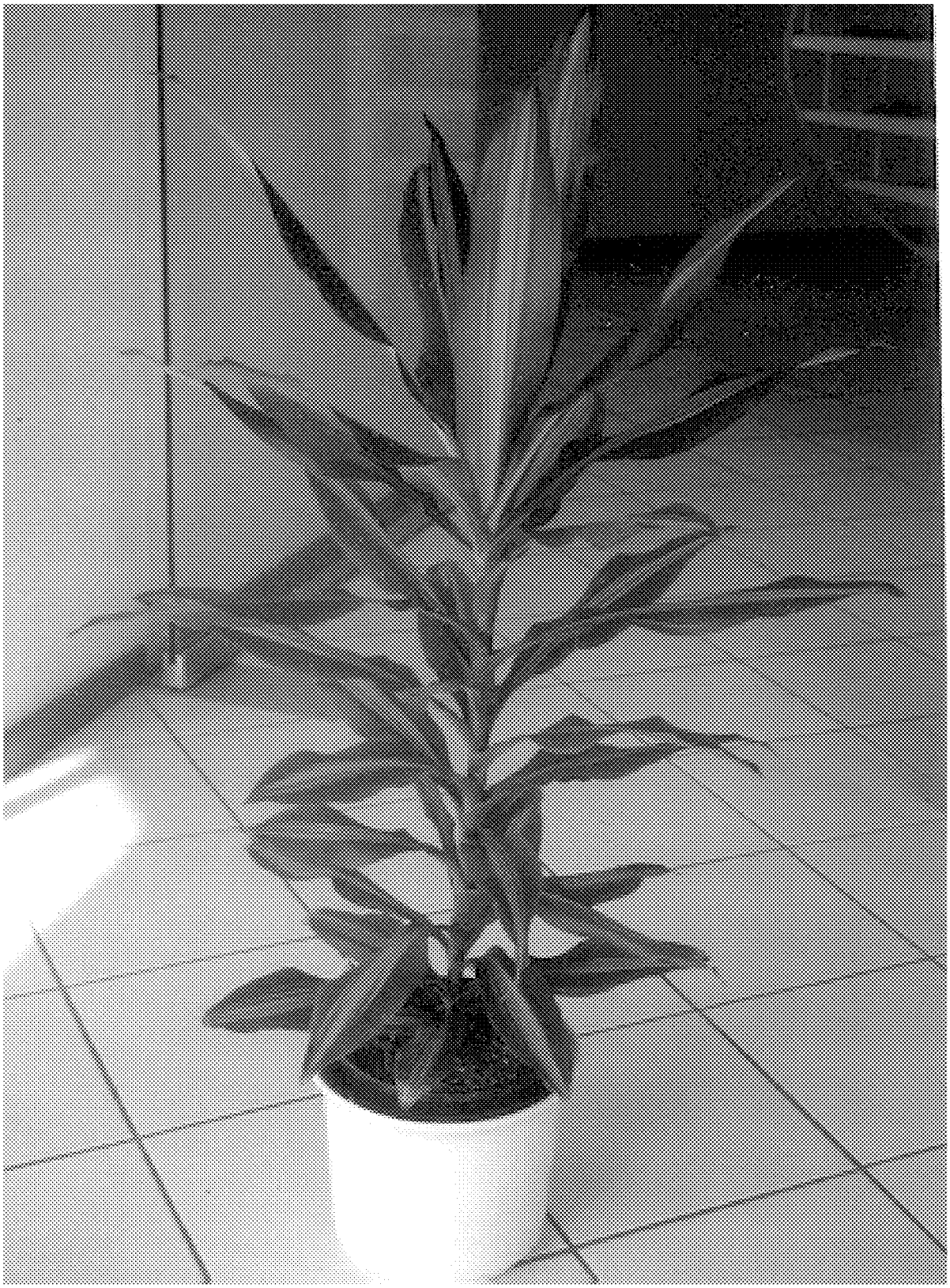

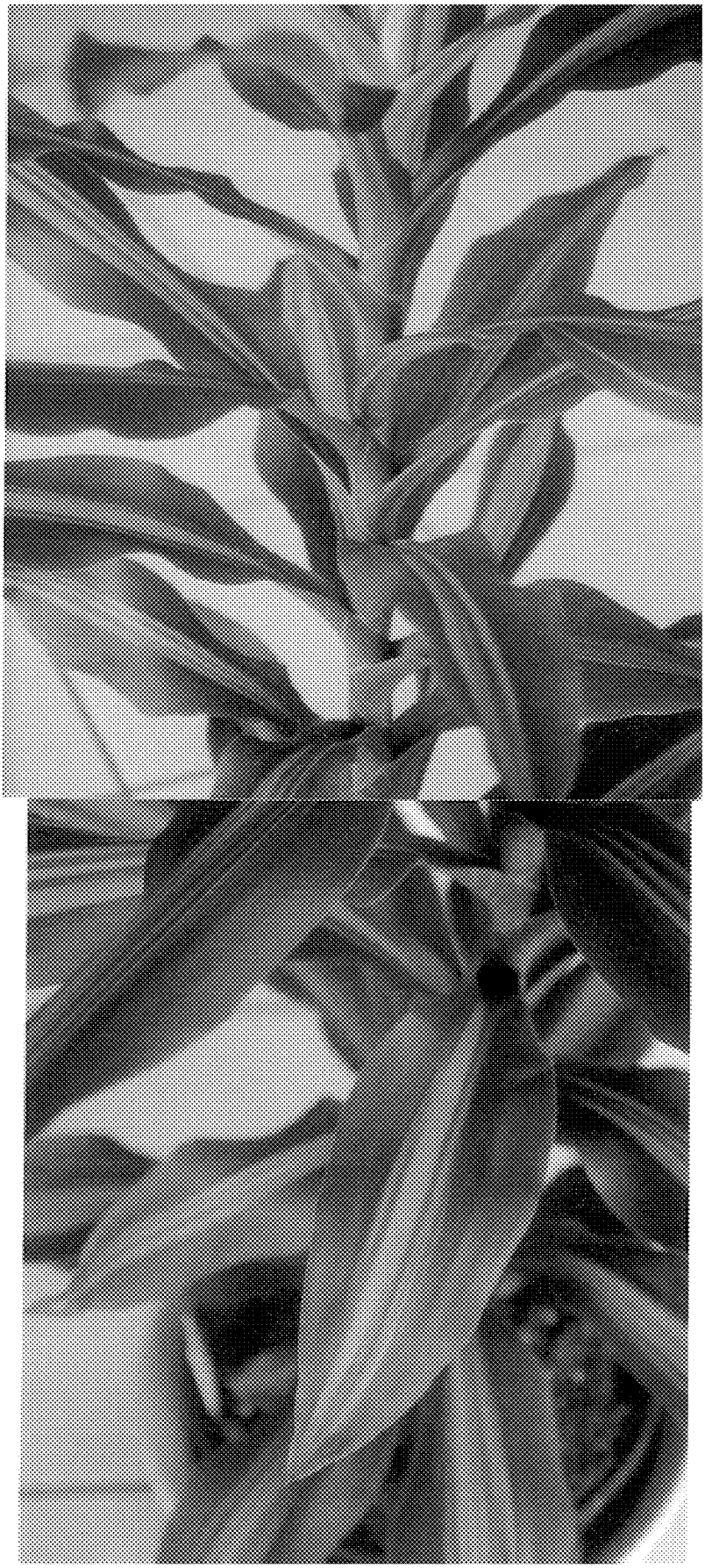

* * * * *